United States Patent
Kundu et al.

(10) Patent No.: US 9,477,701 B1
(45) Date of Patent: Oct. 25, 2016

(54) GENERIC DATA COMPRESSION FOR HEART DIAGNOSIS

(71) Applicant: International Business Machines Corporation, Armonk, NY (US)

(72) Inventors: Tanmoy Kundu, Kolkata (IN); Kaushik Lahiri, Kolkata (IN); Avirup Mandal, Kolkata (IN); Amitava Mukherjee, Kolkata (IN); Mrinal K. Naskar, Kolkata (IN); Sandipan Sinha, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/954,568

(22) Filed: Nov. 30, 2015

(51) Int. Cl.
*G06F 17/30* (2006.01)
*H04W 4/14* (2009.01)
*H04W 88/02* (2009.01)

(52) U.S. Cl.
CPC ... *G06F 17/30371* (2013.01); *G06F 17/30569* (2013.01); *H04W 4/14* (2013.01); *H04W 88/02* (2013.01)

(58) Field of Classification Search
None
See application file for complete search history.

(56) References Cited

U.S. PATENT DOCUMENTS 5,481,255 A * 1/1996 Albert ............... H04W 88/023
340/7.21
2006/0294108 A1* 12/2006 Adelson ............ G06F 19/3456
707/1

OTHER PUBLICATIONS

Lu et al., SPOC: A Secure and Privacy-Preserving Opportunistic Computing Framework for Mobile-Healthcare Emergency, IEEE Transactions on Parallel and Distributed Systems, vol. 24, No. 3, Mar. 2013, pp. 614-624.
Soomro et al., A Framework for Mobile Healthcare Applications over Heterogeneous Networks, 2011 IEEE 13th International Conference on e-Health Networking, Applications and Services, pp. 70-73.
Chiang et al., An Efficient Component-Based Framework for Intelligent Home-Care System Design with Video and Physiological Monitoring Machineries, 2011 Fifth International Conference on Genetic and Evolutionary Computing, pp. 330-336.
A Comparison of Single Lead ECG Data Compression Techniques, http://www.hcs.harvard.edu/~weber/HomePage/Papers/ECGCompression/, Jun. 16, 2015, 8 pages.
Micahel L. Hilton, Wavelet and Wavelet Packet Compression of Electrocardiograms, IEEE Transactions on Biomedical Engineering, vol. 44, No. 5, May 1997, pp. 394-402.

(Continued)

*Primary Examiner* — Son T Hoang
(74) *Attorney, Agent, or Firm* — Schmeiser, Olsen & Watts, LLP; John Pivnichny (57) ABSTRACT

A method and associated systems for generic data compression. A mobile device receives realtime data from a medical-monitoring device, such as a heart monitor, worn by a patient. The invention compresses and encodes this data into ASCII text characters, which are transmitted via a commonly available low-bandwidth text-messaging service, such as the SMS service supported by most cell phones. The text messages are received by a second mobile device, which decodes the text characters into their original form and displays them to a healthcare practitioner. More critical portions of the data are encoded by a high-precision lossless compression mechanism. In some embodiments, the two mobile devices may be cell phones and the second device may have the ability to interpret the decoded information in order to determine whether to directly or indirectly alert the practitioner or other parties of an exceptional condition detected by the medical monitor.

17 Claims, 4 Drawing Sheets

(56) References Cited

OTHER PUBLICATIONS

Djohan et al., ECG Compression Using Discrete Symmetric Wavelet Transform, 1995 IEEE-EMBC and CMBEC, Theme I: Cardiovascular System, pp. 167-168.
Bifulco et al., Bluetooth Portable Device for Continuous ECG and Patient Motion Monitoring During Daily Life, Medicon 2007, IFMBE Proceedings 16, pp. 369-272.
Rezazadeh et al., ECG Data Compression for Mobile Phone Tele-Cardiology Applications Using.NET Framework, 978-1-4244-7000-6/111 copyright 2011 IEEE, pp. 204-207.
Furht et al., An Adaptive Real-Time ECG Compression Algorithm with Variable Threshold, IEEE Transactions on Biomedical Engineering, vol. 35, No. 6, Jun. 1988, pp. 489-494.
Fang et al., A Mobile Device Based ECG Analysis System, Source: Data Mining in Medical and Biological Research, ISBN 978-953-7619-30-5, pp. 320, Dec. 2008, I-Tech, Vienna, Austria, pp. 209-226.
Lascu et al., Electrocardiogram Compression and Optimal Filtering Algorithm, Proceedings of the 7th WSEAS Int. Conf. on Signal Processing, Computational Geometry & Artificial Vision, Athens, Greece, Aug. 24-26, 2007, pp. 193-198.
Rout et al., An Efficient Algorithm for Secure Transmission of Heart Diagnosis Data & Drug Delivery Using WSN, International Journal of Advanced Research in Computer Science and Software Engineering, vol. 3, Issue 2, Feb. 2013, ISSN: 2277 128X, pp. 226-233.
Eli Abbadi et al., New Efficient Technique for Compression of ECG Signal, Copyright, 2013 International Journal of Computer Science Issues, www.IJCSI.org, pp. 139-146.
Abo-Zahhad, et al., ECG Signal Compression Technique Based on Discrete Wavelet Transform and QRS-Complex Estimation, Signal Processing—An International Journal (SPIJ), vol. 4, Issue 2, pp. 138-160.
Lee et al., A Real-Time ECG Data Compression and Transmission Algorithm for an e-Health Device, IEEE Transactions on Biomedical Engineering, vol. 58, No. 9, Sep. 2011, pp. 2448-2455.
Sadak et al., Real-Time ECG Transmission From Multi-Patent Toward Multi-Physician Using Wireless Communications Technologies, Journal of Theoretical and Applied Information Technology, Mar. 31, 2011, vol. 25, No. 2, pp. 98-102.
Das et al., QRS Detection Algorithm Using Savitzky-Golay Filter, Proc. of Int. Joint Colloquium on Emerging Technologies in Computer Electrical and mechanical 2011, pp. 56-59.

\* cited by examiner

GENERIC DATA COMPRESSION FOR HEART DIAGNOSIS

TECHNICAL FIELD

The present invention relates to compressing and translating data gathered by a medical monitoring device into text characters that may be transmitted through a wireless network.

BACKGROUND

Medical devices, such as heart monitors, electrocardiograms, or Holter devices, may provide greater benefit if they can be worn by a patient at all times as a wireless mobile device. Because they must continuously monitor one or more bodily functions with great precision, they may generate large amounts of real-time data, often in the form of a continuously varying high-resolution waveform. Transferring such data in a timely manner and with robust error correction through a wireless communications medium thus requires a high-bandwidth network and proprietary protocols, making it cumbersome, resource-intensive, and expensive to provide reliable realtime performance.

BRIEF SUMMARY

A first embodiment of the present invention provides a generic data-compression system comprising a processor, a memory coupled to the processor, two or more communications interfaces, at least one of which is wireless, and a computer-readable hardware storage device coupled to the processor and containing program code configured to be run by the processor via the memory to implement a method for generic data compression, the method comprising:

the processor directly or indirectly receiving data captured by a medical-monitoring device, wherein the monitoring device monitors a physical condition of a patient, wherein the received data characterizes the monitored physical condition, and wherein the processor receives the data through a first interface of the two or more communications interfaces;

the processor transforming the received data, wherein the transforming comprises encoding the received data into a sequence of ASCII characters; and the processor transmitting the sequence of ASCII characters to a target device through a second interface of the two or more communications interfaces, wherein the transmitting is performed by means of a wireless text-messaging protocol, and wherein the target device is configured to reverse the transforming in order to extract from the ASCII characters a reproduction of the data captured by the medical-monitoring device.

A second embodiment of the present invention provides method for generic data compression, the method comprising:

a processor of a generic data-compression system that comprises two or more communications interfaces directly or indirectly receiving data captured by a medical-monitoring device, wherein the monitoring device monitors a physical condition of a patient, wherein the received data characterizes the monitored physical condition, and wherein the processor receives the data through a first interface of the two or more communications interfaces;

the processor transforming the received data, wherein the transforming comprises encoding the received data into a sequence of ASCII characters;

the processor transforming the received data, wherein the transforming comprises encoding the received data into a sequence of ASCII characters; and the processor transmitting the sequence of ASCII characters to a target device through a second interface of the two or more communications interfaces, wherein the transmitting is performed by means of a wireless text-messaging protocol, and wherein the target device is configured to reverse the transforming in order to extract from the ASCII characters a reproduction of the data captured by the medical-monitoring device.

A third embodiment of the present invention provides a computer program product, comprising a computer-readable hardware storage device having a computer-readable program code stored therein, the program code configured to be executed by a generic data-compression system comprising a processor, a memory coupled to the processor, two or more communications interfaces, at least one of which is wireless, and a computer-readable hardware storage device coupled to the processor and containing program code configured to be run by the processor via the memory to implement a method for generic data compression, the method comprising:

the processor directly or indirectly receiving data captured by a medical-monitoring device, wherein the monitoring device monitors a physical condition of a patient, wherein the received data characterizes the monitored physical condition, and wherein the processor receives the data through a first interface of the two or more communications interfaces;

the processor transforming the received data, wherein the transforming comprises encoding the received data into a sequence of ASCII characters;

the processor transforming the received data, wherein the transforming comprises encoding the received data into a sequence of ASCII characters; and the processor transmitting the sequence of ASCII characters to a target device through a second interface of the two or more communications interfaces, wherein the transmitting is performed by means of a wireless text-messaging protocol, and wherein the target device is configured to reverse the transforming in order to extract from the ASCII characters a reproduction of the data captured by the medical-monitoring device.

DETAILED DESCRIPTION

Embodiments of the present invention may be used to compress and transmit data across a text-based communications medium, such as an SMS (Short Message Service) component of a phone, Web, cellular, or mobile communication system. Examples and embodiments described herein generally describe implementations in which a real-time medical monitor, such as a heart monitor, electrocardiogram (ECG), or Holter monitor (a portable monitoring device that may be used as an ECG or an electroencephalograph), must transmit waveforms through a cell-phone's SMS communications medium to a doctor or hospital. But these examples should not be construed to limit the invention to such monitors, to medical applications, or to SMS networks. Many other types of applications are possible in other fields, and transmitting data generated by other types of devices through other types of wireless or tethered networks.

Most of the exemplary embodiments described here comprise software running on a mobile device, such as a cell phone or a tablet, that is connected via a wired or wireless connection to a medical monitor, and that can transmit data to another mobile device via common wireless protocols, such as SMS or any of the IEEE 802 wireless LAN protocols. Such embodiments may, for example, receive real-time data generated by an ECG or EEG, compress and translate that data into ASCII text characters, and transmit those characters as text messages across a low-bandwidth, low-latency, high-accuracy network (such as an SMS component of a cellular service) to another cell phone, tablet, or other mobile device in the possession of a physician, healthcare aid, or nurse. The received text data is then decompressed back into its original form, such as a sequence of heart-monitor waveforms. Other embodiments may use a similar methodology to transmit data to a network or server of a hospital or medical-alert service.

In this way, embodiments of the present invention allow 7×24 realtime or near-realtime monitoring of a patient and can alert a healthcare professional of an exceptional condition almost immediately via a low-cost, ubiquitous wireless communications medium. Unlike wireless monitors that require proprietary communications mechanisms or high-bandwidth wireless infrastructures, the present invention may provide secure, fast, and accurate communications over a commonly used, standard medium protected by widely adopted data-verification and security mechanisms.

Figure 1:
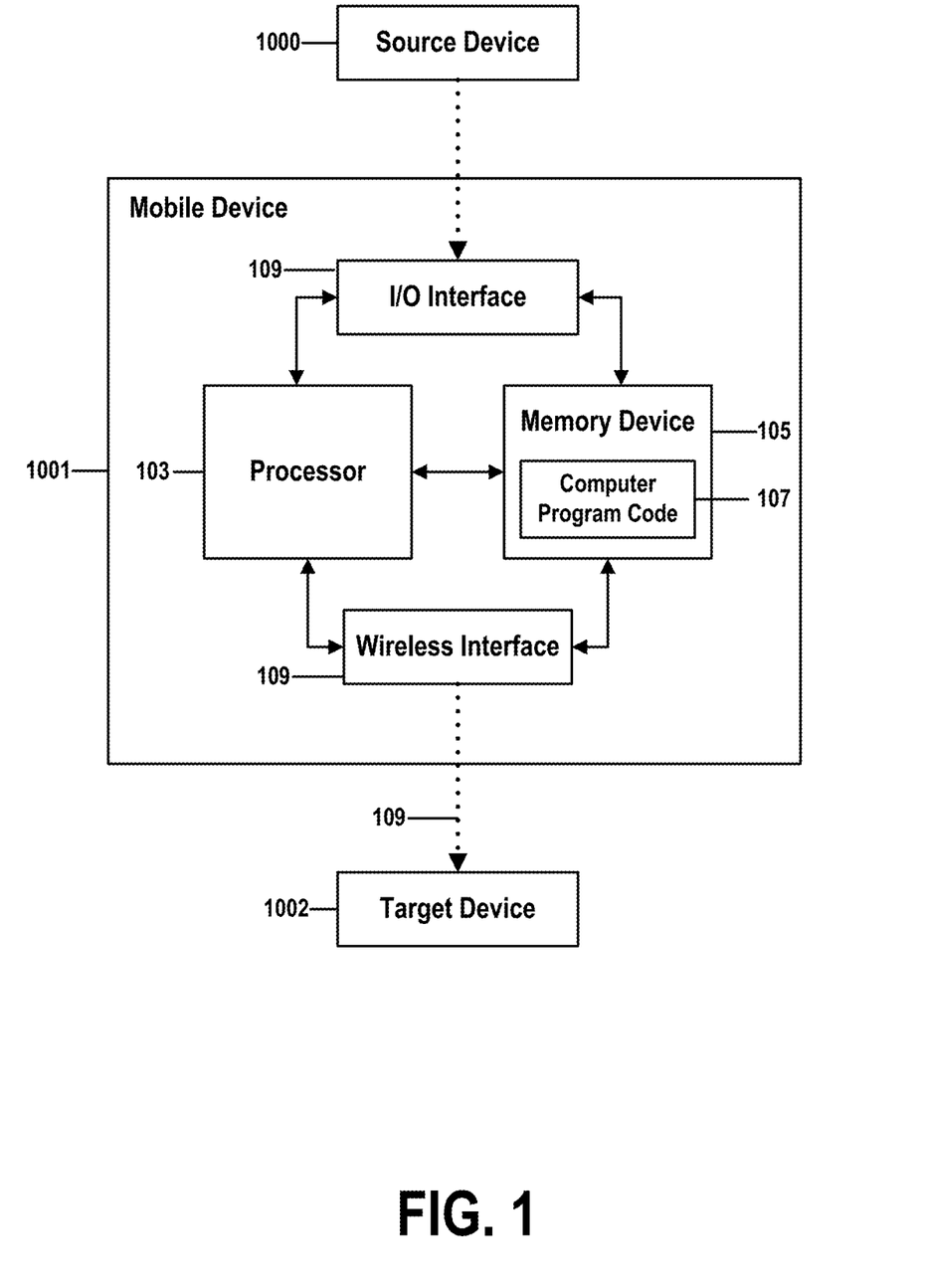
FIG. 1 shows a structure of a computer system and computer program code that may be used to implement a method for generic data compression in accordance with embodiments of the present invention.

FIG. 1 shows a structure of a computer system and computer program code that may be used to implement a method for generic data compression in accordance with embodiments of the present invention. FIG. 1 refers to objects 101-113 and 1000-1002.

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

FIG. 1 shows an example of a system that incorporates an embodiment of the present invention. Components of this system comprise a data-generating source device 1000, a data-processing and communications module 1001, and a target device 1002 that receives and further manipulates data transmitted by module 1001.

In embodiments described herein, module 1001 may be a mobile or wireless device, such as a smartphone, cell phone, tablet-computing device, or notebook computer. Such a device may receive data from source device 1000 through a physical, tethered, or wired connection, or through a wireless connection, such as a wireless local-area network or a Bluetooth network. Target device 1002 may also be a mobile or wireless device that, in some cases, may be similar to module 1001, but in some embodiments may be a server computer or another type of physical or virtual device connected to module 1001 by a wireless, tethered, or virtual infrastructure, or by a combination thereof In one example, source device 1000 might be a wearable heart monitor, such as a Holter device, that transmits waveform data in real time via a Bluetooth network to a smartphone 1001. Aspects of the present invention may incorporate a software app running on the smartphone 1001, where that app compresses and translates the data received by device 1001 through the Bluetooth network into a stream of 8-bit ASCII-encoded alphanumeric characters. In such an embodiment, these alphanumeric text characters are then transmitted via the smartphone through a common SMS text-messaging service to a second smartphone 1002, which receives the characters and then decodes them back into their original waveforms, where they may be viewed by a user of the smartphone 1002.

Many other variations of this basic mechanism are possible. Such variations may, for example, combine a data-generating source 1000 and mobile device 1001 into a single module, or may use different types of wireless or wired communications media to connect devices 1000 and 1001 or to connect devices 1001 and 1002. In some cases, protocols and services other than SMS may be used to transmit the compressed, encoded ASCII characters. But in all cases, embodiments of the present invention incorporate the basic concept of compressing high-bandwidth or realtime data into ASCII-encoded alphanumeric characters that may be transmitted efficiently and accurately over common, industry standard communications infrastructure.

In the example of FIG. 1, mobile device 1001 may comprise one or more computer processors 103 coupled through one or more I/O interfaces 101 and wired or wireless communications media or networks 111 to one or more data-generating source devices 1000. The processors 103 may further be coupled through one or more wireless interfaces 109 and one or more wireless communications media or networks 113 to one or more target devices 1002.

Mobile device or module 1001 may further contain memory or hardware storage devices 105 that stores computer program code 107 for performing a method of generic data compression as described in the figures and below. Memory or storage devices 105 may be further connected to interfaces 101 or 109 in embodiments in which the interfaces have direct memory access to stored computer instructions or data.

Memory or hardware data storage devices 105 may include, but are not limited to, a combination of magnetic tape drives, fixed or removable hard disks, optical discs, storage-equipped mobile devices, and solid-state random-access or read-only storage devices.

Memory or hardware data storage devices 105 may also include, but are not limited to, a combination of one or more Dynamic RAM (DRAM), Static RAM (SRAM), Programmable Read-Only Memory (PROM), Field-Programmable Gate Arrays (FPGA), Secure Digital memory cards, SIM cards, and other types of memory devices capable of storing computer instructions or data.

At least one memory or storage device 105 contains stored computer program code 107, which is a computer program that comprises computer-executable instructions. The stored computer program code includes a program that implements a method for generic data compression in accordance with embodiments of the present invention, and may implement other embodiments of the present invention, as described in this specification, including the methods illustrated in FIGS. 2-4. Computer program code 107 stored in the memory or storage devices 105 is configured to be executed by processor 103.

In some embodiments, rather than being stored and accessed from a recordable or rewritable memory or storage device 105, stored computer program code 107 may be stored on a static, nonremovable, read-only storage medium such as a Read-Only Memory (ROM) device 105, or may be accessed by processor 103 directly from such a static, nonremovable, read-only medium 105. Similarly, in some embodiments, stored computer program code 107 may be stored as computer-readable firmware 105, or may be accessed by processor 103 directly from such firmware 105, rather than from a dynamic or removable hardware data-storage device, such as a hard drive or optical disc.

In such cases, device 1001 may be configured via hardware or firmware to specifically perform methods of the present invention, rather than being a general-purpose processor capable of performing a wide range of programmable operations.

The present invention may further comprise a process for supporting computer infrastructure, integrating, hosting, maintaining, and deploying computer-readable code 107 into a computerized device or system 1001, wherein the code in combination with the device or system 1001 is capable of performing a method for generic data compression.

Any of the components of the present invention could be created, integrated, hosted, maintained, deployed, managed, serviced, supported, etc. by a service provider who offers to facilitate a method for generic data compression. Thus the present invention may comprise a process for deploying or integrating computing infrastructure, comprising integrating computer-readable code into the device or system 1001, wherein the code in combination with the computer system 1001 is capable of performing a method for generic data compression.

One or more data storage units 105 (or one or more additional memory devices not shown in FIG. 1) may be used as a computer-readable hardware storage device having a computer-readable program embodied therein and/or having other data stored therein, wherein the computer-readable program comprises stored computer program code 107. Generally, a computer program product (or, alternatively, an article of manufacture) of computer system 1001 may comprise the computer-readable hardware storage device.

While it is understood that program code 107 for generic data compression may be deployed by manually loading the program code 107 directly into client, server, or proxy computers, devices, or infrastructure components (not shown) by loading the program code 107 into a computer-readable storage medium (e.g., removable storage discs or cards that may be configured into a mobile device 1001 or that may be comprised by computer data storage 105), program code 107 may also be automatically or semi-automatically deployed into computer system 1001 by sending program code 107 to a central server or to a group of central servers. Program code 107 may then be downloaded into client computers or devices (not shown) that will execute program code 107.

The first step of the aforementioned integration of code included in program code 107 is to identify any software on the clients and servers, including the network operating system (not shown), where program code 107 will be deployed that are required by program code 107 or that work in conjunction with program code 107. This identified software includes the network operating system, where the network operating system comprises software that enhances a basic operating system by adding networking features. Next, the software applications and version numbers are identified and compared to a list of software applications and correct version numbers that have been tested to work with program code 107. A software application that is missing or that does not match a correct version number is upgraded to the correct version.

A program instruction that passes parameters from program code 107 to a software application is checked to ensure that the instruction's parameter list matches a parameter list required by the program code 107. Conversely, a parameter passed by the software application to program code 107 is checked to ensure that the parameter matches a parameter required by program code 107. The client and server operating systems, including the network operating systems, are identified and compared to a list of operating systems, version numbers, and network software programs that have been tested to work with program code 107. An operating system, version number, or network software program that does not match an entry of the list of tested operating systems and version numbers is upgraded to the listed level on the client computers and upgraded to the listed level on the server computers.

After ensuring that the software, where program code 107 is to be deployed, is at a correct version level that has been tested to work with program code 107, the integration is completed by installing program code 107 on the clients and servers.

Embodiments of the present invention may be implemented as a method performed by a processor of a computer system, as a computer program product, as a computer system, or as a processor-performed process or service for supporting computer infrastructure.

Figure 2:
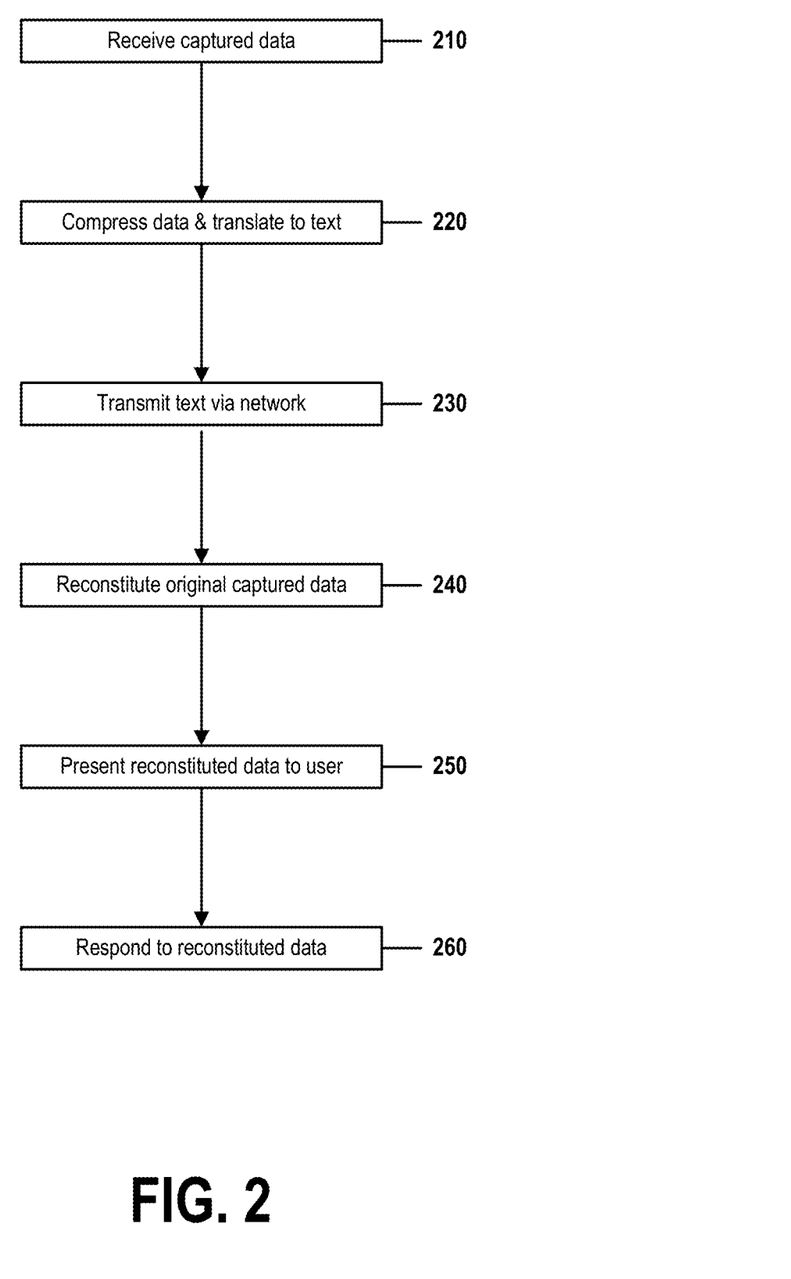
FIG. 2 is a flow chart that illustrates steps of a method for generic data compression in accordance with embodiments of the present invention.

FIG. 2 is a flow chart that illustrates steps of a method for generic data compression in accordance with embodiments of the present invention. FIG. 2 comprises steps 210-260.

In step 210, computerized mobile or wireless device 1001 receives captured data from a data-generating source module 1000. In some embodiments, the data-generating source 1000 may be a wearable or portable heart monitor or other type of device capable of monitoring a medical parameter of a patient, such as a Holter device. In some embodiments, source 1000 may be a fixed or transportable device worn by or otherwise connected to a patient, such as a portable EEG machine.

Source module 1000 may collect realtime patient data and transmit it as a stream of raw data, as a graphical object like a waveform, or as a continuous stream of small windows or packets of data, each of which may represent all or part of a logical object, such as a waveform.

In some embodiments, this captured data may be augmented or complemented by other types of data or metadata, such as the patient's physical location, a periodic or asynchronous time-stamp that identifies when each data sample was collected, or patient metadata that specifies the patient's identify, account information, medical history, medication or treatment protocol, or other facts that may be useful to a healthcare practitioner or medical facility.

This data may be transmitted to computerized device 1001 by means of any communications or networking method known in the art. In one example, data-generating module 1000 may be a wireless heart monitor that is worn continuously by an ambulatory patient. This monitor produces a continuous waveform that represents the patient's heartbeat and transmits that data as a continuous sequence of data blocks, each of which represent a segment of the waveform. These blocks may be transmitted to and received by computerized device 1001 in correct chronological order, but if transmitted through a packet-switching network, they may be transmitted out of order and then properly resequenced upon receipt.

In this example, the heart monitor 1000 and computerized receiving module 1001 may connect through a secure channel of a wireless personal-area network that conforms to the common Bluetooth set of network standards by "pairing" modules 1000 and 1001 prior to transmission.

In some embodiments, this transmission may employ a known health-device protocol, such as the HDP protocol, which is based on the standard ISO/IEEE 11073-20601 protocol stack) and is designed specifically for secure and accurate transmission of a patient's medical data.

In this example, the receiving computerized device 1001 may be a smartphone, a wearable smartwatch (such as the Apple Watch), tablet-computing device, or other portable or wearable device that supports the same communications mechanism used by the data-generating device 1000.

Receiving device 1001 may, for example, be a smartphone that uses the Android operating system and includes a set of Java APIs that can be used to perform communications tasks such as setting up Bluetooth network, scanning for and pairing with other Bluetooth devices, or managing an exchange of data with such devices.

In step 220, the wireless or mobile module 1001 parses, compresses, and translates the received data into a set of alphanumeric characters. In some embodiments, this procedure greatly reduces the volume of data that was received from monitor 1000, thus reducing bandwidth requirements necessitated by further transmission of the compressed data. These methods of parsing, compressing, and translating are described in greater detail in FIGS. 3-4.

In some cases, the complementary or augmenting metadata may also be compressed, translated, or encoded, but in some embodiments, this metadata may have already been received as text and, accordingly, further processing may not be necessary in order to forward it to target device 1002 as text.

In step 230, the wireless or mobile module 1001 transmits the alphanumeric characters generated in step 220 to a target device 1002 by means of an efficient communications mechanism designed for or optimized for transmission of text objects or messages.

In our previous example, step 230 may be performed by smartphone 1001, which encodes the data received in step 210 into bytes of data that conform to the ASCII (American Standard Code for Information Interchange) character set and then transmits these ASCII-encoded characters to a second smartphone 1002 by means of the low-bandwidth SMS (Short Message Service) text-messaging service supported by most cellular phones.

In step 240, the target device 1002 reverses the compression and encoding procedure of step 220 in order to transform the received text messages back into the original representation of data generated by the source device 1001 in step 210. In some embodiments, target device 1002 may merely forward the received text messages to a second device that then restores the text messages to their original representation, as received in step 210.

In step 250, target device 1002, or a device that has received data from target device 1002, may present the reconstituted data to a user or transmit it to a decision-making module for further processing in step 260.

In step 260, the target device 1002, or a device that directly or indirectly received data from target device 1002, determines whether action needs to be taken in response to a characteristic of the reconstituted data generated in step 240. Such an action might, for example, comprise a combination of: alerting a physician, nurse, home health aide, or other practitioner of an emergency condition; notifying a hospital's or third-party's healthcare system, medical device, software application, or other automated entity of an exceptional condition; or recording a change in a patient's medical condition or physical location.

In our ongoing example, the second smartphone 1002, which may be in the possession of a physician, may in step 240 translate its received text messages back into representations of the original waveforms captured by heart monitor 1000. The phone may then, in step 250, notify the physician that a medical-alert message has been received and display the reconstituted waveforms to the physician.

In one variation, if the physician is in a hospital when the message is received, the phone may forward the received text to a server or other communications or processing device integrated into the hospital's computing infrastructure, allowing that hospital device to reconstitute the waveform, to analyze the resulting waveform, and to determine whether an aspect of the waveform requires that the physician be sent an alert, that a nurse or health aid be notified, or that some other action take place.

In some embodiments, the target device 1002 may be the hospital server or other device, rather than the physician's (or other healthcare practitioner's) smartphone. In such cases, the first smartphone 1001 may communicate directly with the hospital resource, allowing the hospital to determine whether the physician need be made aware of a characteristic of the data received in step 210.

Figure 3:
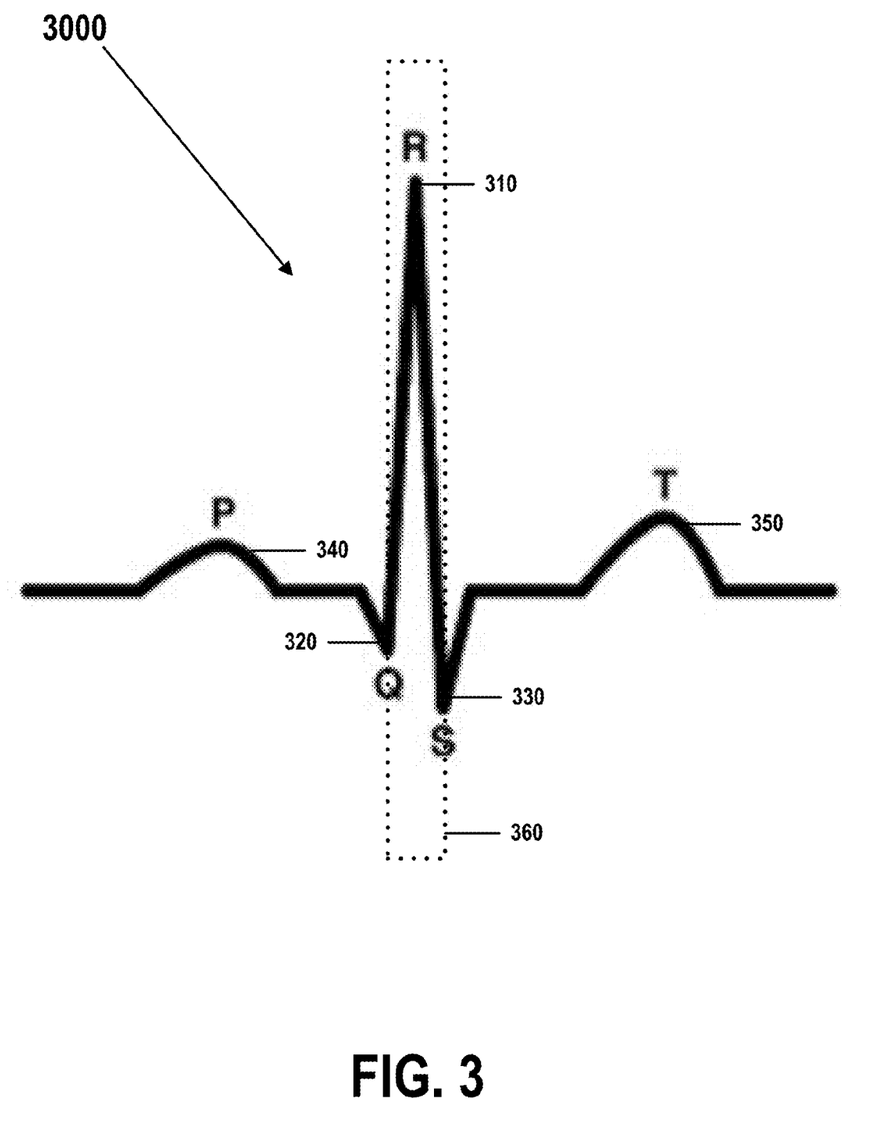
FIG. 3 shows regions of an exemplary signaling waveform captured by a heart monitor.

FIG. 3 shows regions of an exemplary signaling waveform 3000 captured by a heart monitor. FIG. 3 comprises elements 3000 and 310-360.

The morphology of waveform 3000 is typical of waveforms that may be compressed and transformed into ASCII characters by embodiments of the present invention described in this document. Waveform 3000, for example, includes a high-precision "QRS complex" region that should be reproduced with greater precision than other areas of the waveform. This variable level of precision is a unique feature of embodiments described here.

The present invention is not, however, limited to waveforms that depict a patient's heartbeat, or that contain only one region that requires higher-precision reproduction or only two regions that do not require higher-precision reproduction. Other embodiments may be used to compress other types of waveforms, or other types of data gathered by a source device 1000 and communicated to data-compression device 1001, as described in FIGS. 1 and 2. Such other types of waveforms may include a brainwave waveform of an electroencephalograph or a non-medical waveform like an output of a seismograph or a digital-audio or video signal. Yet other embodiments may be used to compress and encode data that might not normally represent a graphical waveform.

Figure 4:
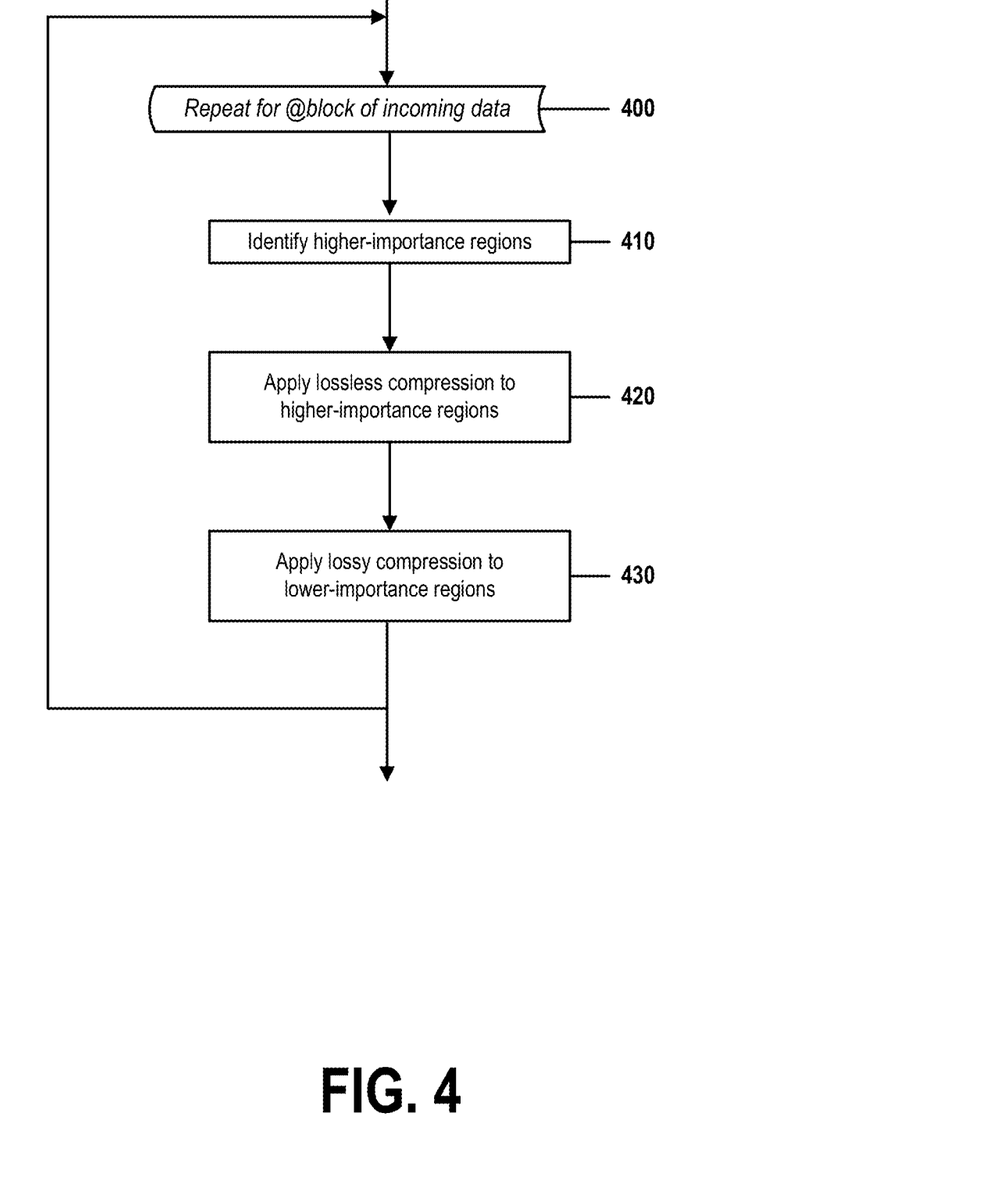
FIG. 4 is a flow chart that elaborates step 220 of FIG. 2 and shows a method of compressing and encoding data in accordance with embodiments of the present invention.

The waveform 3000 of FIG. 3, which will be referenced by examples of FIGS. 2 and 4, comprises a central "QRS" region (delineated by the dotted-line boundary 360), also known as a "QRS complex," and bounded by the initial attack Q 320 and final decay S 330 points of the waveform's central spike.

The duration, amplitude, and shape of the QRS complex 360, as defined by peak-amplitude R 310 and points Q 320 and S 330, are useful in diagnosing heart disease states like cardiac arrhythmias, conduction abnormalities, ventricular hypertrophy, myocardial infarction, electrolyte derangements, and other disease states. It is thus important that the waveform region 360 be reproduced as accurately as a possible. As described in FIGS. 2 and 4, embodiments of the present invention may use a more accurate lossless compression mechanism when compressing a digital representation of QRS complex 260.

The regions of waveform 3000 outside of the bounded QRS region 260 may require less-precise reproduction in certain applications, and may thus lend themselves to lossy compression algorithms, which can have higher compression rations than lossless algorithms. Embodiments of the present invention may thus run more efficiently by using a lossy compression algorithm to compress the region to the left of QRS complex 260 (characterized by point P 340) and the region to the right of QRS complex 260 (characterized by point T 350).

In many cases, a waveform like waveform 3000 may be formed by measuring level of an electrical signal as often as several thousand times a second. Although the details may vary, in some real-world implementations, a waveform 3000 may be represented in digital form by a thousand samples per second, each of which is capable of representing any of 2000 possible voltage levels. Such signals may be difficult to transmit, compress, and decompress in realtime, or at speeds close to realtime, when being processed over small mobile devices and wireless networks. This is especially true of waveforms and regions of waveforms like the QRS complex 260 of FIG. 3, which may be unacceptably degraded by use of a more efficient lossy compression algorithm. As the precision and resolution of medical monitors and other data-generating devices increases, such burdens may become even greater.

FIG. 4 is a flow chart that elaborates step 220 of FIG. 2 and shows a method of compressing and encoding data in accordance with embodiments of the present invention. FIG. 4 comprises steps 400-430.

In some embodiments, step 400 begins an iterative procedure, in which the mobile or wireless device 1001 in each iteration performs the compresses and encodes a single block of data selected or extracted from the stream or entire set of data that the device 1001 received in step 210. In this way, the entire continuous stream of data received in step 210 may be processed and then forwarded to target device 1002, one block at a time. The examples discussed in the description of the method of FIG. 4 refer to a block of data that corresponds to a representation of one heartbeat cycle detected and recorded by a heart monitor, such as the waveform 3001 of FIG. 3. In these examples, this heartbeat representation is extracted from a continuous ECG-like waveform produced by a heart monitor 1000.

In other embodiments, a block of data may be defined as a data set that represents a different logical or structural entity, such as a set of heartbeats, an activity recorded during a specific period of time, or a number of periods of a certain type of periodic waveform.

In other embodiments, the method of FIG. 4 may be performed once for all the data received in step 210, compressing and encoding that data for transmission as a single extended block of text. In such cases, a method of FIG. 2 may be performed iteratively and, in such embodiments, the method of FIG. 2 may be triggered by a receipt of data from a source device 1000, may begin at specified times, may be started manually, or may be initiated by other means.

In the example of FIG. 4, the iterative procedure begun in step 400 continues through step 430, and repeats until the entire body of data received in step 210 has been compressed and encoded into ASCII text. At the conclusion of the final iteration, the method returns to step 230 of FIG. 2. In other embodiments, where the method of FIG. 4 compresses and encodes a single block of data (that is, the method of steps 410-430 are not performed iteratively during the procedure of FIG. 4) and step 230 transmits that single block of encoded data to target device 1002, FIG. 4 and step 230 may themselves form an iterative procedure that is repeated once for each block of data selected or extracted from the data received in step 210.

Other variations of these structures are possible within the scope of the present invention. All of them, however, must in some way process, or at least decided whether to process, every block of data comprised by the set of data received in step 210.

In some cases, the selected or extracted blocks may be extracted, compressed, encoded, and forwarded to target device 1002 in a chronological or sequential order similar or identical to the order in which they were received by device 1001 in step 210. But in other embodiments, they may be processed or forwarded in a different order, so long as they are reassembled in their original order by target device 1002 such that they can be used to represent the original data captured by source device 1000.

In the further description of the method of FIG. 4, we will describe examples in which each block of data corresponds to one In step 410, the wireless or mobile device 1001 identifies one or more higher-precision regions of the block of data currently being processed. In our ongoing example, this block of data, as shown in FIG. 3, comprises an especially important QRS complex region 360 which is bounded by inflection points Q 320 and S 330 and comprises a peak value R 310. The wireless or mobile device 1001 thus performs step 410 in order to identify this QRS region.

In a simple example to illustrate one such procedure, consider block of x data samples that comprises voltage samples VT[n], recorded respectively at times T[n], where a value of n ranges from 1 through x.

Here, we compare each voltage value VT[n] with its preceding value in order to determine whether each VT[n] is part of an increasing or a decreasing portion of the waveform of QRS region 360.

A voltage value VT[n] recorded at time n is thus determined to be an R peak 310 if:

$$(VT[n]-VT[n-1])2>\Delta VR\text{-Threshold}$$

where $\Delta V_{R\text{-}Threshold}$ is a minimum difference in voltage necessary to indicate a height of an R peak 310. In this example, we identify R-peak voltage VT[n] as $VT_{rp}$, where p=a position in the waveform at time T[n] that identifies a position of R peak 310. Here, we arbitrarily define a 120-millisecond region on each side of $VT_{rp}$ and spanning a range of time p-120 ms through p+120 ms. The lower boundary of this 240 ms region is thus deemed to be point Q 320 and the upper boundary to be S 330, thus identifying the higher-precision QRS complex region 360 to be the 240 ms region centered on the voltage $VT_{rp}$ (or VT[n]) that identifies QRS peak R 310.

In our example, this QRS region 360 will be compressed with a more-accurate lossless compression algorithm because it contains the most significant data required for detecting heart related diseases.

In other embodiments, the size, timing, duration, or other characteristics of one or more higher-importance ranges may be identified in a similar or analogous manner. In patients known to suffer from certain coronary conditions, for example, a method of step 410 may be used to identify a narrower QRS range that spans less than 240 ms. In another example, a lower threshold value $\Delta V_{R\text{-}Threshold}$ may be selected in step 410 to more accurately detect weaker heartbeats.

In all cases, however, device 1001 in step 410 will use analytic or graphical techniques to select one or more points or regions of interest in a block of data currently being analyzed.

In step 420, the wireless or mobile device 1001 applies a higher-accuracy lossless compression to the higher-importance region of the data block identified in step 410.

This lossless compression mechanism, which is a novel part of the present invention, comprises the following steps. For pedagogical purposes, we describe here a simple example of this compression mechanism that processes eight consecutive voltage samples stored in an array as variables V[0] . . . V[7].

1. Replace each value V[n] by the value (V[n]−V[n−1]), where 0<n<8. This replaces each voltage (except for the first one) with what is likely to be a smaller value that identifies a difference between the voltage at time n and its previous value at time (n−1).

This procedure would, for example, replace the following eight voltage values:
V=[−375, −390, −400, −400, −385, −305, −140, 100]
with the values:
V=[−375, −15, −10, 0, 15, 80, 165, 240]

2. Store the sign of each new voltage value as a bit of an 8-bit array S, where S[n]=1 if a corresponding V[n]<0, and S[n]=1 if V[n]>=0. Then convert this 8-bit variable into a Base-10 integer.

In the preceding example, 8-bit array S thus would become:
S=[1, 1, 1, 0, 0, 0, 0, 0]=$224_{10}$ 3. Replace each value V[n] by its absolute value |V[n]|. In our running example, V thus becomes:
V=[375, 15, 10, 0, 15, 80, 165, 240]

4. Divide V[0] by 255, replace V[0] by the remainder of this division, and store the quotient as an integer variable Q. This step ensures that the value of V[0] falls within the range of 0 through 255, thus ensuring that it may be represented as an ASCII character.

In our example, array V now stores the values:
V=[120, 15, 10, 0, 15, 80, 165, 240]
Q=1

5. Create and initialize to zero a 5-bit ASCII correction array CorrVars, each bit of which will identify whether a "special-correction" operation (described below) correct a value of any of five variables generated during the current compression procedure.
CorrVars=[ 0 0 0 0 0]

The special-correction operation determines whether an eight-bit integer value may be represented as a printable or displayable ASCII character that is compatible with embodiments of the present invention and, if not, applies a numeric correction to the value that converts it to such a character. The special-correction operation performs this operation upon an eight-bit integer value I by means of the following rules:
(i) IF I∈{10, 13, 26, 255}
THEN I=(I−1)
(ii) IF 128≤I≤159
THEN I=(I+32)
(iii) ELSE I=I (no correction applied)

6. Create and initialize to zero an 8-bit correction array CorrPos, each bit of which will identify whether the special-correction operation will need to correct a corresponding value of any of the eight V[n] values stored in array V.
CorrPos=[0 0 0 0 0 0 0 0]

7. Apply the special-correction operation to Base-10 integer S and store a value of 1 or 0 in the 1st position of correction array CorrVars, where the value of this stored value is determined by whether S required special correction.

In the ongoing example, the special-correction operation determines that no correction was necessary for Base-10 value S. The first position of CorrVars is thus set to 0:
CorrVars=[ 0 0 0 0 0]

8. Apply the special-correction operation to each of the eight V[i] values stored in array V (that is, apply the operation to each V[i] where 0<=i<8). Store a value of 1 or 0 in each position of the 8-bit binary array CorrPos, where the value of an $n^{th}$ value stored in CorrPos is determined by whether a corresponding value of V[n] requires special correction. Convert the resulting 8-bit CorrPos data structure to its equivalent Base-10 integer value.

In the ongoing example, the special-correction operation determines that only V[2]=10 required correction. Only the corresponding third bit of CorrPos is thus set to 1:
CorrPos=[0 0 1 0 0 0 0 0]=$32_{10}$ 9. Apply the special-correction operation to decimal value CorrPos and store a value of 1 or 0 in the 2nd position of correction array CorrVars, where the value of this stored value is determined by whether CorrPos requires correction.

In our example, the special-correction algorithm determines that CorrPos (value=32) does not require correction. The second bit of array CorrVars thus remains set to 0.
CorrVars=[0 0 0 0 0]

10. Group each pair of adjacent (V[n],V[n+1]) values of array V into a single value g[n], and associate that value g[n] with one of three groups, a Right group, a Left group, or an Ungrouped group, according to the following rule:
For 0<=n<=6:
IF (V[n]*100+V[n+1])<255
THEN g[n]=(V[n]*100+V[n+1]) (Right group)
ELSE IF (V[n]+V[n+1]*100)<255
THEN g[n]=(V[n]+V[n+1]100) (Left group)
ELSE g[n]=V[n] otherwise (Ungrouped group)

In our ongoing example, where array V now contains values:
V=[120, 15, 10, 0, 15, 80, 165, 240],
we determine a value of each g[n] and associate each g[n] according to the above rules:

| n | V[n] | V[n + 1] | V[n] * 100 + V[n + 1] | V[n] + V[n + 1] * 100 | Group |
|---|------|----------|----------------------|----------------------|-------|
| 0 | 120  | 15       | 12015                | 1620                 | U     |
| 1 | 15   | 10       | 1510                 | 1015                 | U     |
| 2 | 10   | 0        | 1000                 | 10                   | L     |
| 3 | 0    | 15       | 15                   | 1500                 | R     |
| 4 | 15   | 80       | 1580                 | 8015                 | U     |
| 5 | 80   | 165      | 8165                 | 16580                | U     |
| 6 | 165  | 240      | 16740                | 24165                | U     |

11. Store the position of each Right group value in a first 8-value bit array named RGRP by setting the $n^{th}$ bit of the array to 1 to indicate that a corresponding value of g[n] is associated with the Right group.

Store the position of each Left group value in a second 8-value bit array named LGRP by setting the $n^{th}$ bit of the array to 1 to indicate that a corresponding value of g[n] is associated with the Left group.

Store the position of each Ungrouped value in a third 8-value bit array named UNGRP by setting the $n^{th}$ bit of the array to 1 to indicate that a corresponding value of g[n] is associated with the Ungrouped group.

Convert each of these bit arrays to a Base-10 integer number.

In our ongoing example, these three bit arrays thus assume the values:

LGRP=[0 0 1 0 0 0 0 0]=$32_{10}$
RGRP=[0 0 0 1 0 0 0 0]=$16_{10}$
UNGRP=[1 1 0 0 1 1 1 0]=$206_{10}$

12. Apply the special-correction operation to the three Base-10 integers LGRP, RGRP, and UNGRP and store a value of 1 or 0 in the third, fourth, and fifth positions of correction array CorrVars, where the value of each of these stored value=0 if the special-correction operation determines that the corresponding integer value does not require correction, and the value of each of these stored value=1 if the special-correction operation determines that the corresponding integer value does require correction.

In our example, none of the above Base-10 values LGRP, RGRP, and UNGRP need correction, resulting in setting the last three bits of CorrVars to zero values:

CorrVars=[0 0 000]

13. Convert CorrVars into a Base-10 integer value and apply the special-correction operation to the resulting value. If the special-correction operation determines that the Base-10 integer value of CorrVars does not require correction, then set a binary variable R to a zero value. If the special-correction operation determines that the Base-10 integer value of CorrVars does require correction, then set variable R to a value of 1.

In our example, CorrVars=0 and thus does not require correction by the special-correction operation. Thus:

R=0

14. LGRP, RGRP, UNGRP, CorrPos, CorrVars, and each grouped voltage value g[n] now all contain integer values within a range that may be represented as a printable ASCII characters. Furthermore, variables R and Q may be arithmetically combined into an 8-bit printable ASCII character equal to a value (R*100)+Q.

Together, these variables contain a highly compressed, lossless record of all the data necessary to reconstitute the vital characteristics of the original higher-precision QRS region 360 of the block of data identified in step 410. Furthermore, the arithmetic procedure described above to generate these variables is computationally simple and requires so little computing power that it may be performed in realtime by even a simple handheld mobile device like a cell phone.

Because these variables may now be interpreted as printable ASCII characters, they are now ready to be transmitted to target device 1002 by means of a common low-overhead wireless text-messaging services such as SMS, thus obviating a need to use proprietary networking methods or communications hardware.

In step 430 the wireless or mobile device 1001 applies a less-accurate lossy compression algorithm to one or more lower-importance regions of the data block being processed by the current iteration of the iterative procedure of FIG. 4. These lower-importance regions may be identified by any means known to those skilled in the art, or they may be selected as regions not identified as having higher importance in step 410.

As in the description of the lossless compression algorithm of step 420, we describe here for pedagogical purposes a simple example of the lossy compression mechanism that processes a small number of consecutive voltage samples. In this example, we compress 16 values, which represent P 340 and T 350 regions of a heartbeat waveform 3000 that fall outside the higher-importance QRS complex region 360. In other implementations, device 1001 may in step may process other regions of other types of waveforms, graphical objects, or data sets. But in all cases, the data that is selected, compressed, and encoded by the lossy algorithm of step 430 is deemed to require less precision or to be less critical than the data that is selected, compressed, and encoded by the lossless algorithm of step 420.

Wireless or mobile device 1001 performs these lossy-compression and encoding tasks on each 16-sample block of data comprised by one or more of these less-critical regions by means of the following steps:

1. Store the set of sixteen consecutive voltage values in 16-element array V as V[0], V[1], . . . V[15]). One example of values stored in such an array V is:

V=(V[0], V[1], . . . V[15})=
V=[−1, 4, 12, 9, 4, 4, 4, 8, 19, 6, 14, −−5, −8, 2, 14, −6]

2. Discard the even-position values of V by successively replacing each V[n] with V[2n+1], where 0≤n<8, and then converting V to an eight-element array by discarding the eight highest-position data elements. This step immediately reduces the information content and storage requirements of the sampled data by 50%, at the cost of cutting its resolution in half.

In our example, this step would convert V into an 8-tuple that contains the values V[0] . . . V[7]:

V=[4, 9, 4, 8, 6, −5, 2, −6]

3. As in step 420, store the sign of each voltage value V[0] . . . V[7] as a bit of an 8-bit array S, where S[n]=1 if a corresponding V[n]<0, and S [n]=1 if V[n]>=0. Then convert this 8-bit variable into a Base-10 integer.

In the previous example, at the conclusion of this step, S would contain:

S=[0, 0, 0, 0, 0, 1, 0, 1]=$5_{10}$

4. Replace each value V[n] in array V by the absolute value of V[n]|V[n]|.

In our example, V becomes;

V=[4, 9, 4, 8, 6, 5, 2, 6]

5. Create and initialize to zero a 5-element ASCII-correction bit-array CorrVars, each bit of which will identify whether the special-correction operation described above in step 420 has corrected a value of any of six variables that will be generated during the current lossy compression procedure.

CorrVars=[0 0 0 0 0]

6. Apply the special-correction operation described above in step 420 to the Base-10 integer value S and store a value of 1 or 0 in the 1st position of correction array CorrVars, where, as in step 420, a value of this stored value is determined by whether S required special correction.

In this example, because the 224 Base-10 value of S does not require correction, the first position of the CorrVars array retains its initial zero value.

CorrVars=[0 0 0 0 0]

7. Transform the eight voltage values V[0] . . . V[7] into four grouped values G[0] . . . G[3] by applying the following formula:

$$G(n)=(V[2n]*10)+V[2n+1], 0≤n<4$$

In our ongoing example this step generates four new grouped values G[0] . . . G[3], where:

$G[0]=10*4+9=49$ $G[1]=10*4+8=48$ $G[2]=10*6+5=65$ $G[3]=10*2+6=26$ and $G=[49,48,65,26]$ 8. Apply the special-correction operation to these four grouped values G[0] . . . G[3] and store 1 or 0 values in the 2nd, 3rd, 4th, and 5th positions of CorrVars respectively to indicate, as above, whether correction was applied to each corresponding grouped value G[0] . . . G[3].

In our running example, correction did not need to be applied to any of values G[0] . . . G[3], resulting in:
CorrVars=[0 0001]

9. Convert CorrVars into a Base-10 integer equivalent, apply the special-correction operation to this Base-10 integer, and, as before, indicate whether correction was applied to CorrVars by storing a 1 or a 0 in a binary variable R.

In our example:
CorrVars=$1_{10}{\rightarrow}R=0$

10. As in step 14 of the lossless-compression algorithm above, all the values generated during the performance of the lossy-compression algorithm—S, R, and G[0] . . . G[3]—now contain integer values within a range that may be represented as a printable ASCII characters.

As with the lossless algorithm of step 420, these variables contain a highly compressed record of all the data necessary to create an imperfect, but still useful, representation of the original lower-importance regions of the block of data identified in step 410. Although half of the original voltage values are discarded by the lossy compression mechanism, a satisfactory approximation of these discarded values may be recovered through linear-interpolation techniques known to those skilled in the art.

Furthermore, the arithmetic procedure described above to generate these variables is likely to be even less computationally demanding than that of the lossless algorithm of step 420 and will produce output that is far smaller and that requires less communications bandwidth that that generated by the lossless algorithm.

At the conclusion of step 430 of FIG. 4, the iterative procedure of steps 400-430 will have produced one or more strings of printable ASCI characters that represent with higher accuracy one or more higher-importance regions of the input block of data, one or more strings of printable ASCI characters that represent with somewhat less accuracy one or more lower-importance regions of the input block of data, or a combination thereof If the current embodiment of the method of FIG. 4 is performed iteratively, the iterative procedure of steps 400-430 continues, compressing the next block of data into printable ASCII-encoded characters, and this procedure continues until all relevant data received in step 210 has been so encoded.

The method of the present invention then continues to completion with step 230 of FIG. 2.

What is claim is:

1. A generic data-compression system comprising a processor, a memory coupled to the processor, two or more communications interfaces, at least one of which is wireless, and a computer-readable hardware storage device coupled to the processor and containing program code configured to be run by the processor via the memory to implement a method for generic data compression, the method comprising:

the processor directly or indirectly receiving data captured by a medical-monitoring device, wherein the monitoring device monitors a physical condition of a patient, wherein the received data characterizes the monitored physical condition, and wherein the processor receives the data through a first interface of the two or more communications interfaces;

the processor transforming the received data, wherein the transforming comprises encoding the received data into a sequence of ASCII characters, wherein the transforming comprises encoding into printable ASCII characters, by means of a lossless compression algorithm, information represented by an array V of eight numeric data elements comprised by the received data, wherein the eight data elements are labeled V(0), V(1), V(2), V(3), V(4), V(5), V(6), and V(7) and represent eight consecutive voltage measurements, and wherein the lossless compression algorithm comprises the following steps:

the processor creating an eight-element bit array CorrPos and a five-element bit array CorrVars and initializing all elements of CorrPos and CorrVars to a value of 0;

the processor successively replacing each data element V(n) with a value equal to (V(n)–V(n–1)) for 0<n<=7;

the processor creating an 8-element bit array S of binary variables S(0), S(1), S(2), S(3), S(4), S(5), S(6), and S(7), wherein S(n)=1 if a value of a corresponding V(n) is less than zero and S(n)=0 otherwise;

the processor interpreting the resulting array S as an 8-bit binary representation of a base-10 integer;

the processor replacing each value V(n) stored in array V with an absolute magnitude of value V(n);

the processor dividing the value of V(0) by 255, storing a quotient of this division in an integer variable Q, and replacing the value of V(0) with a remainder of this division;

the processor applying a special-correction operation to the base-10 integer value stored in S, wherein the special-correction operation performs the following steps upon a value to which the operation is applied:

i) if the value to which the operation is applied is 10, 13, 26, or 255, then the processor decrements the value by one and the operation returns a value of 1;

ii) if the value to which the operation is applied inclusively falls within a range of 128 through 159, then the processor adds 32 to the value and the operation returns a value of 1; and iii) otherwise the operation returns a value of 0;

the processor setting the first data element of five-element array CorrVars to a value returned by the special-correction operation performed upon the value stored in S;

the processor further applying the special-correction operation upon each value V(n) stored in array V, 0<=n<=7, and storing a value returned by the special-correction operation upon each value V(n) in a corresponding $n^{th}$ position of eight-element array CorrPos;

the processor interpreting the resulting array CorrPos as an 8-bit binary representation of a base-10 integer;

the processor applying the special-correction operation to the base-10 integer value stored in CorrPos and setting the second data element of five-element array CorrVars to the value returned by the special-correction operation performed upon the value stored in CorrPos;

the processor generating three eight-element bit arrays LGRP, RGRP, and UNGRP and initializing each binary element of these arrays to a value of zero;

the processor generating a seven-element array G, comprising data elements G(0), G(1), G(2), G(3), G(4), G(5), and G(6), wherein each G(n) is set to a value according to the following rules:

i) if (V[n]*100+V[n+1])<255, then the processor sets G(n)=(V[n]*100+V[n+1]) and the processor sets a corresponding $n^{th}$ element of array RGRP to a value of 1;

ii) if (V[n]+V[n+1]*100)<255, then the processor sets G(n)=(V[n]+V[n+1]*100) and the processor sets a corresponding $n^{th}$ element of array LGRP to a value of 1; and iii) Otherwise the processor sets G(n)=v(n) and the processor sets a corresponding $n^{th}$ element of array UNGRP to a value of 1;

the processor interpreting each of the resulting 8-bit values stored in arrays RGRP, LGRP, and UNGRP as an 8-bit binary representation of a base-10 integer;

the processor applying the special-correction operation to the base-10 integer represented by the value stored in array RGRP and setting the third data element of five-element array CorrVars to a value returned by the special-correction operation performed upon the value stored in RGRP;

the processor applying the special-correction operation to the base-10 integer represented by the value stored in array LGRP and setting the fourth data element of five-element array CorrVars to a value returned by the special-correction operation performed upon the value stored in LGRP;

the processor applying the special-correction operation to the base-10 integer represented by the value stored in array UNGRP and setting the fifth data element of five-element array CorrVars to a value returned by the special-correction operation performed upon the value stored in UNGRP;

the processor interpreting the five-bit value stored in array CorrVars as a base-10 integer value and applying the special-correction operation to this base-10 integer value:

the processor setting a binary variable R to a value returned by the special-correction operation performed upon the base-10 representation of the value stored in CorrVars; and the processor encoding into printable ASCII characters the resulting integer values of LGRP, RGRP, UNGRP, CorrPos, CorrVars, each data element G(n), and a value equal to (R*100)+Q; and the processor transmitting the sequence of ASCII characters to a target device through a second interface of the two or more communications interfaces, wherein the transmitting is performed by means of a wireless text-messaging protocol, and wherein the target device is configured to reverse the transforming in order to extract from the ASCII characters a reproduction of the data captured by the medical-monitoring device.

2. The system of claim 1, wherein the medical-monitoring device is selected from a group comprising a Holter device, an electrocardiogram, and an electroencephalograph.

3. The system of claim 1, wherein the transforming comprises encoding into printable ASCII characters, by means of a lossy compression algorithm, sixteen numeric data elements comprised by the received data, wherein the sixteen data elements are labeled D(0), D(1), D(2), D(3), D(4), D(5), D(6), D(7), D(8), D(9), D(10), D(11), D(12), D(13), D(14), and D(15), and represent sixteen consecutive voltage measurements, and wherein the lossy compression algorithm comprises the following steps:

the processor creating an eight-element bit array CorrPos and a five-element bit array CorrVars and initializing all elements of CorrPos and CorrVars to a value of 0;

the processor creating and populating an eight-element numeric array V, comprised of data elements V(0), V(1), V(2), V(3), V(4), V(5), V(6), and V(7), with the respective values of data elements D(1), D(3), D(5), D(7), D(9), D(11), D(13), and D(15);

the processor creating an 8-element bit array S of binary variables S(0), S(1), S(2), S(3), S(4), S(5), S(6), and S(7), wherein S(n)=1 if a value of a corresponding V(n) is less than zero and S(n)=0 otherwise;

the processor interpreting the resulting array S as an 8-bit binary representation of a base-10 integer;

the processor replacing each value V(n) stored in array V with an absolute magnitude of value V(n);

the processor applying a special-correction operation to the base-10 integer value stored in S, wherein the special-correction operation performs the following steps upon a value to which the operation is applied:

i) if the value to which the operation is applied is 10, 13, 26, or 255, then the processor decrements the value by one and the operation returns a value of 1;

ii) if the value to which the operation is applied inclusively falls within a range of 128 through 159, then the processor adds 32 to the value and the operation returns a value of 1; and iii) otherwise the operation returns a value of 0;

the processor setting the first data element of five-element array CorrVars to a value returned by the special-correction operation performed upon the value stored in S;

the processor populating a four-element integer array G, comprised of data elements G(0), G(1), G(2), and G(3), with values computed by a formula G(n)=(V[2n]*10)+V[2n+1], $0 \leq n < 4$;

the processor applying the special-correction operation to the value of G(0) and setting the second data element of five-element array CorrVars to a value returned by the special-correction operation performed upon the value of G(0);

the processor applying the special-correction operation to the value of G(1) and setting the third data element of five-element array CorrVars to a value returned by the special-correction operation performed upon the value of G(1);

the processor applying the special-correction operation to the value of G(2) and setting the fourth data element of five-element array CorrVars to a value returned by the special-correction operation performed upon the value of G(2);

the processor applying the special-correction operation to the value of G(3) and setting the fifth data element of five-element array CorrVars to a value returned by the special-correction operation performed upon the value of G(3);

the processor interpreting the resulting value of five-element array CorrVars as a 6-bit binary representation of a base-10 integer;

the processor applying the special-correction operation to the base-10 integer represented by array CorrVars setting a binary variable R to a value returned by the special-correction operation performed upon the base-10 value represented by CorrVars; and the processor encoding into printable ASCII characters the resulting integer values comprised by variables S and R and array G.

4. The system of claim 1, wherein the wireless text-messaging protocol is the Short Message Service protocol.

5. The system of claim 1, wherein the generic data-compression system and the target system each comprise a smartphone that supports wireless communications over a cellular network.

6. A method for generic data compression, the method comprising:

a processor of a generic data-compression system that comprises two or more communications interfaces directly or indirectly receiving data captured by a medical-monitoring device, wherein the monitoring device monitors a physical condition of a patient, wherein the received data characterizes the monitored physical condition, and wherein the processor receives the data through a first interface of the two or more communications interfaces;

the processor transforming the received data, wherein the transforming comprises encoding the received data into a sequence of ASCII characters, wherein the transforming comprises encoding into printable ASCII characters, by means of a lossless compression algorithm, information represented by an array V of eight numeric data elements comprised by the received data, wherein the eight data elements are labeled V(0), V(1), V(2), V(3), V(4), V(5), V(6), and V(7) and represent eight consecutive voltage measurements, and wherein the lossless compression algorithm comprises the following steps:

the processor creating an eight-element bit array CorrPos and a five-element bit array CorrVars and initializing all elements of CorrPos and CorrVars to a value of 0:

the processor successively replacing each data element V(n) with a value equal to (V(n)−V(n−1)) for $0<n<=7$;

the processor creating an 8-element bit array S of binary variables S(0), S(1), S(2), S(3), S(4), S(5), S(6), and S(7), wherein S(n)=1 if a value of a corresponding V(n) is less than zero and S(n)=0 otherwise;

the processor interpreting the resulting array S as an 8-bit binary representation of a base-10 integer;

the processor replacing each value V(n) stored in array V with an absolute magnitude of value V(n);

the processor dividing the value of V(0) by 255, storing a quotient of this division in an integer variable Q, and replacing the value of V(0) with a remainder of this division;

the processor applying a special-correction operation to the base-10 integer value stored in S, wherein the special-correction operation performs the following steps upon a value to which the operation is applied:

i) if the value to which the operation is applied is 10, 13, 26, or 255, then the processor decrements the value by one and the operation returns a value of 1;

ii) if the value to which the operation is applied inclusively falls within a range of 128 through 159, then the processor adds 32 to the value and the operation returns a value of 1; and iii) otherwise the operation returns a value of 0;

the processor setting the first data element of five-element array CorrVars to a value returned by the special-correction operation performed upon the value stored in S;

the processor further applying the special-correction operation upon each value V(n) stored in array V, $0<=n<=7$, and storing a value returned by the special-correction operation upon each value V(n) in a corresponding $n^{th}$ position of eight-element array CorrPos;

the processor interpreting the resulting array CorrPos as an 8-bit binary representation of a base-10 integer;

the processor applying the special-correction operation to the base-10 integer value stored in CorrPos and setting the second data element of five-element array CorrVars to the value returned by the special-correction operation performed upon the value stored in CorrPos;

the processor generating three eight-element bit arrays LGRP, RGRP, and UNGRP and initializing each binary element of these arrays to a value of zero;

the processor generating a seven-element array G, comprising data elements G(0), G(1), G(2), G(3), G(4), G(5), and G(6), wherein each G(n) is set to a value according to the following rules:

i) if (V[n]*100+V[n+1])<255, then the processor sets G(n)=(V[n]*100+V[n+1]) and the processor sets a corresponding $n^{th}$ element of array RGRP to a value of 1;

ii) if (V[n]+V[n+1]*100)<255, then the processor sets G(n)=(V[n]+V[n+1]*100) and the processor sets a corresponding $n^{th}$ element of array LGRP to a value of 1; and iii) Otherwise the processor sets G(n)=v(n) and the processor sets a corresponding $n^{th}$ element of array UNGRP to a value of 1;

the processor interpreting each of the resulting 8-bit values stored in arrays RGRP, LGRP, and UNGRP as an 8-bit binary representation of a base-10 integer;

the processor applying the special-correction operation to the base-10 integer represented by the value stored in array RGRP and setting the third data element of five-element array CorrVars to a value returned by the special-correction operation performed upon the value stored in RGRP;

the processor applying the special-correction operation to the base-10 integer represented by the value stored in array LGRP and setting the fourth data element of five-element array CorrVars to a value returned by the special-correction operation performed upon the value stored in LGRP;

the processor applying the special-correction operation to the base-10 integer represented by the value stored in array UNGRP and setting the fifth data element of five-element array CorrVars to a value returned by the special-correction operation performed upon the value stored in UNGRP;

the processor interpreting the five-bit value stored in array CorrVars as a base-10 integer value and applying the special-correction operation to this base-10 integer value:

the processor setting a binary variable R to a value returned by the special-correction operation performed upon the base-10 representation of the value stored in CorrVars; and the processor encoding into printable ASCII characters the resulting integer values of LGRP, RGRP, UNGRP, CorrPos, CorrVars, each data element G(n), and a value equal to (R*100)+Q; and the processor transforming the received data, wherein the transforming comprises encoding the received data into a sequence of ASCII characters; and the processor transmitting the sequence of ASCII characters to a target device through a second interface of the two or more communications interfaces, wherein the transmitting is performed by means of a wireless text-messaging protocol, and wherein the target device is configured to reverse the transforming in order to extract from the ASCII characters a reproduction of the data captured by the medical-monitoring device.

7. The method of claim 6, wherein the medical-monitoring device is selected from a group comprising a Holter device, an electrocardiogram, and an electroencephalograph.

8. The method of claim 6, wherein the transforming comprises encoding into printable ASCII characters, by means of a lossy compression algorithm, sixteen numeric data elements comprised by the received data, wherein the sixteen data elements are labeled D(0), D(1), D(2), D(3), D(4), D(5), D(6), D(7), D(8), D(9), D(10), D(11), D(12), D(13), D(14), and D(15), and represent sixteen consecutive voltage measurements, and wherein the lossy compression algorithm comprises the following steps:

the processor creating an eight-element bit array CorrPos and a five-element bit array CorrVars and initializing all elements of CorrPos and CorrVars to a value of 0;

the processor creating and populating an eight-element numeric array V, comprised of data elements V(0), V(1), V(2), V(3), V(4), V(5), V(6), and V(7), with the respective values of data elements D(1), D(3), D(5), D(7), D(9), D(11), D(13), and D(15);

the processor creating an 8-element bit array S of binary variables S(0), S(1), S(2), S(3), S(4), S(5), S(6), and S(7), wherein S(n)=1 if a value of a corresponding V(n) is less than zero and S(n)=0 otherwise;

the processor interpreting the resulting array S as an 8-bit binary representation of a base-10 integer;

the processor replacing each value V(n) stored in array V with an absolute magnitude of value V(n);

the processor applying a special-correction operation to the base-10 integer value stored in S, wherein the special-correction operation performs the following steps upon a value to which the operation is applied:
  i) if the value to which the operation is applied is 10, 13, 26, or 255, then the processor decrements the value by one and the operation returns a value of 1;
  ii) if the value to which the operation is applied inclusively falls within a range of 128 through 159, then the processor adds 32 to the value and the operation returns a value of 1; and
  iii) otherwise the operation returns a value of 0;

the processor setting the first data element of five-element array CorrVars to a value returned by the special-correction operation performed upon the value stored in S;

the processor populating a four-element integer array G, comprised of data elements G(0), G(1), G(2), and G(3), with values computed by a formula G(n)=(V[2n]*10)+V[2n+1], 0≤n<4;

the processor applying the special-correction operation to the value of G(0) and setting the second data element of five-element array CorrVars to a value returned by the special-correction operation performed upon the value of G(0);

the processor applying the special-correction operation to the value of G(1) and setting the third data element of five-element array CorrVars to a value returned by the special-correction operation performed upon the value of G(1);

the processor applying the special-correction operation to the value of G(2) and setting the fourth data element of five-element array CorrVars to a value returned by the special-correction operation performed upon the value of G(2);

the processor applying the special-correction operation to the value of G(3) and setting the fifth data element of five-element array CorrVars to a value returned by the special-correction operation performed upon the value of G(3);

the processor interpreting the resulting value of five-element array CorrVars as a 6-bit binary representation of a base-10 integer;

the processor applying the special-correction operation to the base-10 integer represented by array CorrVars setting a binary variable R to a value returned by the special-correction operation performed upon the base-10 value represented by CorrVars; and the processor encoding into printable ASCII characters the resulting integer values comprised by variables S and R and array G.

9. The method of claim 6, wherein the wireless text-messaging protocol is the Short Message Service protocol.

10. The method of claim 6, wherein the generic data-compression system and the target system each comprise a smartphone that supports wireless communications over a cellular network.

11. The method of claim 6, further comprising providing at least one support service for at least one of creating, integrating, hosting, maintaining, and deploying computer-readable program code in the computer system, wherein the computer-readable program code in combination with the computer system is configured to implement the receiving, transforming, and transmitting.

12. A computer program product, comprising a computer-readable hardware storage device having a computer-readable program code stored therein, the program code configured to be executed by a generic data-compression system comprising a processor, a memory coupled to the processor, two or more communications interfaces, at least one of which is wireless, and a computer-readable hardware storage device coupled to the processor and containing program code configured to be run by the processor via the memory to implement a method for generic data compression, the method comprising:

the processor directly or indirectly receiving data captured by a medical-monitoring device, wherein the monitoring device monitors a physical condition of a patient, wherein the received data characterizes the monitored physical condition, and wherein the processor receives the data through a first interface of the two or more communications interfaces;

the processor transforming the received data, wherein the transforming comprises encoding the received data into a sequence of ASCII characters, wherein the transforming comprises encoding into printable ASCII characters, by means of a lossless compression algorithm, information represented by an array V of eight numeric data elements comprised by the received data, wherein the eight data elements are labeled V(0), V(1), V(2), V(3), V(4), V(5), V(6), and V(7) and represent eight consecutive voltage measurements, and wherein the lossless compression algorithm comprises the following steps:

the processor creating an eight-element bit array CorrPos and a five-element bit array CorrVars and initializing all elements of CorrPos and CorrVars to a value of 0;

the processor successively replacing each data element V(n) with a value equal to (V(n)−V(n−1)) for 0<n<=7;

the processor creating an 8-element bit array S of binary variables S(0), S(1), S(2), S(3), S(4), S(5), S(6), and S(7), wherein S(n)=1 if a value of a corresponding V(n) is less than zero and S(n)=0 otherwise;

the processor interpreting the resulting array S as an 8-bit binary representation of a base-10 integer;

the processor replacing each value V(n) stored in array V with an absolute magnitude of value V(n);

the processor dividing the value of V(0) by 255, storing a quotient of this division in an integer variable Q, and replacing the value of V(0) with a remainder of this division;

the processor applying a special-correction operation to the base-10 integer value stored in S, wherein the special-correction operation performs the following steps upon a value to which the operation is applied:

i) if the value to which the operation is applied is 10, 13, 26, or 255, then the processor decrements the value by one and the operation returns a value of 1;

ii) if the value to which the operation is applied inclusively falls within a range of 128 through 159, then the processor adds 32 to the value and the operation returns a value of 1; and iii) otherwise the operation returns a value of 0;

the processor setting the first data element of five-element array CorrVars to a value returned by the special-correction operation performed upon the value stored in S;

the processor further applying the special-correction operation upon each value V(n) stored in array V, 0<=n<=7, and storing a value returned by the special-correction operation upon each value V(n) in a corresponding $n^{th}$ position of eight-element array CorrPos;

the processor interpreting the resulting array CorrPos as an 8-bit binary representation of a base-10 integer;

the processor applying the special-correction operation to the base-10 integer value stored in CorrPos and setting the second data element of five-element array CorrVars to the value returned by the special-correction operation performed upon the value stored in CorrPos;

the processor generating three eight-element bit arrays LGRP, RGRP, and UNGRP and initializing each binary element of these arrays to a value of zero;

the processor generating a seven-element array G, comprising data elements G(0), G(1), G(2), G(3), G(4), G(5), and G(6), wherein each G(n) is set to a value according to the following rules:

i) if (V[n]*100+V[n+1])<255, then the processor sets G(n)=(V[n]*100+V[n+1]) and the processor sets a corresponding $n^{th}$ element of array RGRP to a value of 1;

ii) if (V[n]+V[n+1]*100)<255, then the processor sets G(n)=+V[n+1]*100) and the processor sets a corresponding $n^{th}$ element of array LGRP to a value of 1; and iii) Otherwise the processor sets G(n)=v(n) and the processor sets a corresponding $n^{th}$ element of array UNGRP to a value of 1;

the processor interpreting each of the resulting 8-bit values stored in arrays RGRP, LGRP, and UNGRP as an 8-bit binary representation of a base-10 integer;

the processor applying the special-correction operation to the base-10 integer represented by the value stored in array RGRP and setting the third data element of five-element array CorrVars to a value returned by the special-correction operation performed upon the value stored in RGRP;

the processor applying the special-correction operation to the base-10 integer represented by the value stored in array LGRP and setting the fourth data element of five-element array CorrVars to a value returned by the special-correction operation performed upon the value stored in LGRP;

the processor applying the special-correction operation to the base-10 integer represented by the value stored in array UNGRP and setting the fifth data element of five-element array CorrVars to a value returned by the special-correction operation performed upon the value stored in UNGRP;

the processor interpreting the five-bit value stored in array CorrVars as a base-10 integer value and applying the special-correction operation to this base-10 integer value;

the processor setting a binary variable R to a value returned by the special-correction operation performed upon the base-10 representation of the value stored in CorrVars; and the processor encoding into printable ASCII characters the resulting integer values of LGRP, RGRP, UNGRP, CorrPos, CorrVars, each data element G(n), and a value equal to (R*100)+Q; and the processor transmitting the sequence of ASCII characters to a target device through a second interface of the two or more communications interfaces, wherein the transmitting is performed by means of a wireless text-messaging protocol, and wherein the target device is configured to reverse the transforming in order to extract from the ASCII characters a reproduction of the data captured by the medical-monitoring device.

13. The computer program product of claim 12, wherein the medical-monitoring device is selected from a group comprising a Holter device, an electrocardiogram, and an electroencephalograph.

14. The computer program product of claim 12, wherein the transforming comprises encoding characters, by means of a lossy compression algorithm, sixteen numeric data elements comprised by the received data, wherein the sixteen data elements are labeled D(0), D(1), D(2), D(3), D(4), D(5), D(6), D(7), D(8), D(9), D(10), D(11), D(12), D(13), D(14), and D(15), and represent sixteen consecutive voltage measurements, and wherein the lossy compression algorithm comprises the following steps:

the processor creating an eight-element bit array CorrPos and a five-element bit array CorrVars and initializing all elements of CorrPos and CorrVars to a value of 0;

the processor creating and populating an eight-element numeric array V, comprised of data elements V(0), V(1), V(2), V(3), V(4), V(5), V(6), and V(7), with the respective values of data elements D(1), D(3), D(5), D(7), D(9), D(11), D(13), and D(15);

the processor creating an 8-element bit array S of binary variables S(0), S(1), S(2), S(3), S(4), S(5), S(6), and S(7), wherein S(n)=1 if a value of a corresponding V(n) is less than zero and S(n)=0 otherwise;

the processor interpreting the resulting array S as an 8-bit binary representation of a base-10 integer;

the processor replacing each value V(n) stored in array V with an absolute magnitude of value V(n);

the processor applying a special-correction operation to the base-10 integer value stored in S, wherein the special-correction operation performs the following steps upon a value to which the operation is applied:

i) if the value to which the operation is applied is 10, 13, 26, or 255, then the processor decrements the value by one and the operation returns a value of 1;

ii) if the value to which the operation is applied inclusively falls within a range of 128 through 159, then the processor adds 32 to the value and the operation returns a value of 1; and         iii) otherwise the operation returns a value of 0;

the processor setting the first data element of five-element array CorrVars to a value returned by the special-correction operation performed upon the value stored in S;

the processor populating a four-element integer array G, comprised of data elements G(0), G(1), G(2), and G(3), with values computed by a formula $G(n)=(V[2n]*10)+V[2n+1]$, $0 \leq n < 4$;

the processor applying the special-correction operation to the value of G(0) and setting the second data element of five-element array CorrVars to a value returned by the special-correction operation performed upon the value of G(0);

the processor applying the special-correction operation to the value of G(1) and setting the third data element of five-element array CorrVars to a value returned by the special-correction operation performed upon the value of G(1);

the processor applying the special-correction operation to the value of G(2) and setting the fourth data element of five-element array CorrVars to a value returned by the special-correction operation performed upon the value of G(2);

the processor applying the special-correction operation to the value of G(3) and setting the fifth data element of five-element array CorrVars to a value returned by the special-correction operation performed upon the value of G(3);

the processor interpreting the resulting value of five-element array CorrVars as a 6-bit binary representation of a base-10 integer;

the processor applying the special-correction operation to the base-10 integer represented by array CorrVars setting a binary variable R to a value returned by the special-correction operation performed upon the base-10 value represented by CorrVars; and     the processor encoding into printable ASCII characters the resulting integer values comprised by variables S and R and array G.

15. The computer program product of claim 12, wherein the wireless text-messaging protocol is the Short Message Service protocol.

16. The computer program product of claim 12, wherein the generic data-compression system and the target system each comprise a smartphone that supports wireless communications over a cellular network.

17. The computer program product of claim 12, further comprising providing at least one support service for at least one of creating, integrating, hosting, maintaining, and deploying computer-readable program code in the computer system, wherein the computer-readable program code in combination with the computer system is configured to implement the receiving, transforming, and transmitting.

* * * * *